US006713074B2

(12) United States Patent
Lerner et al.

(10) Patent No.: US 6,713,074 B2
(45) Date of Patent: Mar. 30, 2004

(54) COSMETIC COMPOSITION AND METHOD

(75) Inventors: David S. Lerner, Boca Raton, FL (US); Gregory Schultz, Gainesville, FL (US)

(73) Assignees: Quick Med Technologies Inc., Gainesville, FL (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/896,566

(22) Filed: Jun. 29, 2001

(65) Prior Publication Data

US 2002/0054922 A1 May 9, 2002

Related U.S. Application Data

(60) Provisional application No. 60/215,087, filed on Jun. 29, 2000.

(51) Int. Cl.[7] .............................. A61K 7/00; A61K 7/42; A61K 31/70; A61K 31/56
(52) U.S. Cl. ........................ 424/401; 424/59; 514/23; 514/24; 514/25; 514/26; 514/33; 514/182
(58) Field of Search ..................... 424/401, 59; 514/23, 514/24, 25, 26, 33, 182

(56) References Cited

U.S. PATENT DOCUMENTS

| 5,665,367 A | * | 9/1997 | Burger et al. ................ 424/401 |
| 5,696,147 A | | 12/1997 | Galardy |
| 5,747,538 A | * | 5/1998 | Meybeck et al. ........... 514/570 |
| 5,773,438 A | | 6/1998 | Levy et al. |
| 5,837,224 A | | 11/1998 | Voorhees et al. |
| 5,885,596 A | | 3/1999 | Parab |
| 5,892,112 A | | 4/1999 | Levy et al. |
| 6,030,620 A | * | 2/2000 | Pillai et al. .................. 514/757 |
| 6,130,254 A | | 10/2000 | Fisher et al. |
| 6,139,828 A | | 10/2000 | McCullough |
| 6,270,780 B1 | * | 8/2001 | Carson et al. ............... 424/401 |
| 6,338,855 B1 | * | 1/2002 | Albacarys et al. ........... 424/409 |
| 6,358,517 B1 | * | 3/2002 | Pillai et al. .................. 424/401 |
| 6,395,281 B1 | * | 5/2002 | Januario et al. ........ 424/195.16 |
| 2002/0010162 A1 | * | 1/2002 | Fleischmajer ................ 514/152 |

FOREIGN PATENT DOCUMENTS

| EP | 1000613 A | 5/2000 |
| WO | WO 00/37107 | 6/2000 |

* cited by examiner

Primary Examiner—Michael G. Hartley
Assistant Examiner—Marina Lamm
(74) Attorney, Agent, or Firm—Gerard H. Bencen

(57) ABSTRACT

The cosmetic topical formulation of this invention is directed toward diminishing skin wrinkling, fine line, improving skin tone, and combinations thereof. Preferably, the topical formulation contains a matrix metalloproteinase inhibitor, MMPI, and advantageously includes a natural estrogen, e.g., a true estrogen compound, such as 17-beta estradiol, or an estrogen-like steroid, (such as various phytoestrogens found in herbal preparations), as opposed to a synthetic estrogen. Other forms of the cosmetic topical formulation of this invention include combinations of synthetic estrogen and MMP inhibitor. Exemplary synthetic estrogens include, but are not limited to, ethinyl estradiol and clomiphine citrate. The cosmetic topical formulation is safe and effective diminishing wrinkling, and improving skin tone. Certain compositions of this invention are useful for minimizing photodamage to skin, while in other embodiments, the composition according to this invention is useful to prevent or minimize the adverse effects on skin induced by cigarette smoking.

4 Claims, No Drawings

COSMETIC COMPOSITION AND METHOD

CROSS REFERENCE TO RELATED APPLICATIONS

This application is a non-provisional continuation-in-part of provisional patent application Ser. No. 60/215,087, filed Jun. 29, 2000.

FIELD OF THE INVENTION

This invention provides a composition and method for reducing or preventing wrinkling and damage of skin upon topical application.

BACKGROUND OF THE INVENTION

As women go through menopause and men age, both experience increased skin wrinkling and decreased skin thickness. Until recently, the molecular mechanism responsible for these skin changes was not well understood. In post-menopausal women, the decreasing levels of plasma estrogen obviously plays a role in the process, but estrogen's influence on the molecular pathways that lead to skin wrinkling and skin thinning was not recognized until recently. Ascroft et al. reported that oral estrogen replacement therapy reversed the delay in healing of skin biopsy wounds observed between pre-menopausal women and healthy post-menopausal women. (See G. S. Ascroft et al, "Estrogen Accelerates Cutaneous Wound Healing Associated with an Increase in TGF-$\beta$1," Nature Medicine 3:1209–1215, 1997; Ascroft et al., "Human Ageing Impairs Injury-induced in Vivo Expression of Tissue Inhibitors of Matrix Metalloproteinases (TIMP-1 and -2 Proteins and mRNA," J. Pathol. 183:169–176, 1997; Ascroft et al., "Age-Related Changes in the Temporal and Spatial Regulation of Matrix Metalloproteinases (MMP) Protein and mRNA Profiles in Normal Skin and Acute Cutaneous Wounds of Healthy Humans," Cell tissue Res. 290:581–591, 1997). In addition, they reported that systemic estrogen replacement therapy increased the level of transforming growth factor protein and decreased the levels of matrix metalloproteinases in wound sites. This discovery led Ascroft, et al., to hypothesize that systemic estrogen replacement therapy stimulated production of TGF-$\beta$1, which is known to stimulate synthesis of extracellular matrix proteins including collagen and simultaneously decreases the production of matrix metalloproteinase. The result of these combined effects of estrogen was to promote healing of the full-thickness punch wounds in the skin of post-menopausal women.

In a subsequent paper, Ascroft et al., investigated the effects of topical estrogen treatment in aged humans. (Ascroft et al., "Topical Estrogen Accelerates Cutaneous Wound Healing in Aged Humans Associated with an Altered Inflammatory Response," Am. J. Pathol. 155:1137–1146, 1999). The skin punch biopsy model was utilized as before, but instead of placing the patients on oral estrogen replacement therapy or not, aged men (average age of 70 years old), and women (average age of 74 years old) were randomized to receive either estrogen (25 micrograms estradiol per 24 hours) delivered topically by a skin patch placed over the wound or placebo. Compared to placebo, topical estrogen treatment increased the extent of wound healing in both males and females with a decrease in wound size at day 7, increased collagen levels at both days 7 and 80, and increased fibronectin levels at day 7.

Taken together, these studies indicate that systemic or topical estrogen may improve healing of full-thickness skin wounds in aged men and women, by increasing the levels of TGF-$\beta$1 which in turn increases synthesis of collagen and simultaneously decreases levels of matrix metalloproteinases.

In U.S. Pat. No. 6,130,254, methods for inhibiting photoaging of skin are disclosed. The method disclosed includes the use of UVA and UVB blockers in combination with an MMP inhibitor, such as a retinoid. In one composition, a composition comprising a retinoid in combination with a flavone or isoflavone compound was disclosed and claimed for application to the skin at least eight hours prior to exposure to the sun.

None of the art identified by the present inventors includes the combination of a MMPI, and an estrogen or phytoestrogen for long-term, daily application to reduce the effects of aging on skin (wrinkling, fine lines, loss of tone, and the like). The present invention provides a solution that meets this need. In addition, in specific compositions according to this invention, combinations of non-retinoid MMP inhibitors, and non-flavone or isoflavone phytoestrogens are used in combination with known UVA and UVB blockers to treat, including to reverse, reduce, prevent or avoid aging photoaging of skin, including fine lines and wrinkles in skin.

SUMMARY OF THE INVENTION

The cosmetic topical formulation of this invention is directed toward diminishing skin wrinkling, improving skin tone, or both. Preferably, the topical formulation contains a matrix metalloproteinase inhibitor, MMPI, and advantageously includes a natural estrogen, e.g., a true estrogen compound, such as 17-beta estradiol, or an estrogen-like steroid, (such as various phytoestrogens found in herbal preparations), as opposed to a synthetic estrogen. Other forms of the cosmetic topical formulation of this invention include combinations of synthetic estrogen and MMP inhibitor. Exemplary synthetic estrogens include, but are not limited to, ethinyl estradiol and clomiphine citrate. The cosmetic topical formulation is safe and effective in diminishing wrinkling, and improving skin tone. In specific formulations, the composition of this invention may furthermore be used to reduce or reverse photoaging or cigarette smoking induced wrinkling or fine lines that occurs in living human skin.

DETAILED DESCRIPTION OF THE PREFERRED EMBODIMENTS OF THIS INVENTION

In one exemplary embodiment of the present invention, a combination of a natural or synthetic estrogen with an MMP inhibitor, such as Ilomostat, is provided in a topical formulation for use as a cosmetic anti-wrinkle cream. The combination of the estrogen and the MMP inhibitor synergistically promotes deposition of new extracellular matrix and reduces its turnover, resulting in the reduction in wrinkling and thinning associated with normal skin aging. In addition, the method and composition according to this invention is useful in limiting the degree of skin wrinkling, fine lines and aging associated with cigarette smoking, cigar smoking, second hand smoke exposure, and the like, bum victims, fire-fighters, and others exposed to smoke.

The matrix metalloproteinase inhibitors (MMPIs) for use according to this invention include, but are not limited to, those MMPI compounds disclosed and claimed in U.S. Pat. Nos. 5,892,112; 5,773,438; 5,696,147, all of which are hereby incorporated herein by reference. Ilomostat is one preferred MMPI.

Collagen molecules provide the major tensile strength of the skin. As a person ages, protein components in the extracellular matrix of the dermis, such as collagen molecules, become degraded. As a result, the skin begins to sag, wrinkle, and thin. The second component of the present topical formulation, the MMP inhibitor, addresses this problem. A preferred MMP-inhibitor is Ilomostat, which is a small, modified dipeptide and an extremely potent inhibitor of the major classes of MMPs present in the skin including collagenases, gelatinases, and stromelysins. Ilomostat also has the desirable property of being amphipathic, which means that it has both hydrophobic and hydrophilic properties. Therefore, Ilomostat can diffuse through the hydrophobic keratinized layers of the epidermal layer of the skin, and also interact with the proteases that are present in the water-filled extracellular matrix of the dermis. Although the topical formulation includes Ilomostat, other MMP inhibitors (natural or synthetic or both) may be used in other embodiments of the topical formulation, such as tissue inhibitors of metalloproteinases (TIMP), Galardin, Batimastat, Marimastat or any hydroxamate-based synthetic inhibitors.

As discussed above, the topical formulation is a cosmetic composition, as opposed to a prescription drug. The cosmetic topical formulation of this invention is directed toward diminishing skin wrinkling, skin tone, or both. Preferably, the topical formulation includes an MMPI, and also advantageously includes a natural estrogen, e.g., a true estrogen compound, such as 17-beta estradiol, or an estrogen-like steroid, (such as various phytoestrogens found in herbal preparations), as opposed to a synthetic estrogen. Other forms of the cosmetic topical formulation of this invention include combinations of synthetic estrogen and MMP inhibitor. Exemplary synthetic estrogens include, but are not limited to, ethinyl estradiol and clomiphine citrate. In preferred compositions according to this invention, an extract of a plant rich in plant compounds having estrogen or estrogen-like activity is combined with the MMPI. Thus, in one specific embodiment of this invention, the plant extract is an extract of black cohosh, (Cimicifuga racemosa), which has been shown to contain a variety of triterpene glycosides (see, for example, Shao, et al., J. Nat. Prod., 2000, 63, 905–910, herein incorporated by reference for this purpose). In the present invention disclosure, we demonstrate that a composition comprising triterpene glycosides, a known class of phytoestrogens, in combination with a known MMPI results in dramatic reduction in skin wrinkling.

The cosmetic topical formulation is safe and effective for diminishing wrinkling, and improving skin tone. Known carriers for the skin are various creams, gels and solutions, many of which are adapted for facilitating transdermal penetration of the biologically effective agent included in the applied composition.

Compositions according to this invention, in addition to the foregoing compositions, which are intended for daily usage, without regard to exposure to the sun, may include compositions for diminishing, avoiding, or preventing photoaging of skin. As noted, in U.S. Pat. No. 6,130,254, certain compositions and methods of use thereof, were disclosed, comprising retinoids for reducing the degree of MMP expression in response to exposure to sunlight, in combination with flavone or isoflavone compounds. In addition, the composition contained UVA and UVB blockers. The disclosure of the U.S. Pat. No. 6,130,254 patent is hereby incorporated by reference for the purpose of providing known compositions comprising UVA and UVB blockers. However, compositions of the present invention that are adapted for application to the skin prior to exposure to the sun include direct inhibitors of matrix metalloproteinases, as described above, rather than indirect suppressors of matrix metalloproteinase expression. As a result, the present composition may be applied to the skin in a time frame much more proximate to the anticipated exposure to sun than the eight hours disclosed as being optimal according to the U.S. Pat. No. 6,130,254 patent. In addition, compositions of this invention which are adapted for reducing photoaging of the skin comprise estrogen, synthetic estrogen, phytoestrogens other than flavones or isoflavones, such as the triterpene glycosides present in plant extracts, such as black cohosh.

As disclosed herein, testing of the cosmetic topical formulation of this invention has been conducted on volunteers and the effects of the composition on wrinkling was scored. Embodiments of the present invention are found to dramatically increase the tone and reduce wrinkling of skin by either visual inspection or photomicrograhic analysis.

In a further exemplary embodiment of this invention, a prescription topical formulation is prepared, based on similar principles to those described above, except in higher dosages than for the cosmetic formulation described above. The prescription formulation, like the cosmetic formulation, includes an MMP inhibitor in combination with at least one natural or synthetic estrogen or both.

Those skilled in the art will appreciate that a wide variety of cosmetic vehicles may be employed according to the present invention. For example, the vehicle may be a simple combination of a buffered solution of propylene glycol, and an acrylate gelation agent, or any of a wide variety of known or commercially available cream or gel formulations. In a further composition according to this invention, a carrier is included which itself has been shown to have beneficial effects for wrinkle reduction. Thus, for example, the carrier may be that disclosed according to U.S. Pat. No. 5,885,596, hereby incorporated by reference. According to that patent, a composition comprising about 40% by weight of water; up to about 35% by weight, of a permeation enhancing compound selected from the group consisting of dibutyl adipate, isopropyl myristate and combinations thereof; up to about 15% by weight of a fatty alcohol; and one or more emollients or moisturizing humectants. As disclosed in the '596 patent, such a carrier, containing no active agents, has a significant anti-wrinkle effect. According to the present invention, in one embodiment, the carrier disclosed according to the '596 patent, or an equivalent thereof, is combined with the active agents as disclosed herein, namely an MMPI and an estrogen, or phytoestrogen. Furthermore, UVA and UVB blocking agents, such as those disclosed according to the U.S. Pat. No. 6,130,254 patent, may be included to provide a composition effective at preventing, minimizing or avoiding photoaging.

For each component, an effective amount is that amount correlative with the amount of matrix metalloproteinase, and estrogen, phytoestrogens or both, consistent with reduction in wrinkling required in a given time period. The ratio of MMPI to estrogen/phytoestrogen in the composition might be in the range of about 1000:1 to about 1:1000 on a molar basis, so long as at least an additive effect is noted as compared to use of the MMPI alone or the estrogenic compound alone. Other desirable ratios include, but are not limited to 100:1 to about 1:100, 10:1 to about 1:10, and about 1:1 ratios, all of which may be verified by routine experimentation based on the present disclosure. Concentrations of about 10 ng/mL to about 100 mg/mL of the MMPI are preferred. Preferably, the estrogen or phytoestrogen is present in the composition at a concentration of about 10 ng/mL to about 100 mg/mL, depending on such routinely defined parameters as solubility and dose response requirements for prevention or reduction of skin wrinkling.

In light of the general disclosure provided herein above, with respect to the manner of practicing this invention, and the manner of making the composition according to this invention, those skilled in the art will appreciate that this invention enables the practice of the invention as defined in the attached claims. However, the following experimental details are provided to ensure a complete written description of this invention, including of the best mode thereof. However, it will be appreciated that the scope of this invention should not be construed in terms of the specific examples provided. Rather, the scope of this invention is to be apprehended with reference to the claims appended hereto, in light of the complete description of this invention constituted by this entire invention disclosure.

EXAMPLE 1

Cosmetic Composition Comprising Ilomastat and Black Cohosh

A composition comprising black cohosh extract at 15 ml of extract per 100 grams of gel and 10 mg of Ilomastat and 100 ml of generic cream carrier comprising 35% propylene glycol and the balance water and an acrylate gellant was formed by thorough mixing. The cream was applied to the forearms and then face and neck of a volunteer.

EXAMPLE 2

Effects of the Composition According to this Invention in Vivo

A volunteer applied the composition according to Example 1 twice a day to the inside of his forearms with about 0.5 cc of the composition for one week. Once it was determined that the composition was well tolerated, a similar treatment was conducted on the volunteer's face around the orbit.

EXAMPLE 3

In Vivo Treatment Using the Composition of this Invention

A composition containing of 10 mg Ilomastat per 100 ml and 2 ml of concentrated black cohosh extract to a carrier comprising 35% propylene glycol and the balance water and an acrylate gellant was formed by thorough mixing. Female volunteers applied the gel to their face for 3 weeks. Photographs were taken before, during, and after the test period.

EXAMPLE 4

Results of in Vivo Treatment

We have completed the 4-week Independent Photomicrographic and Visual Evaluation Testing of the wrinkle reducing effect of Ilomastat & black cohosh. We empanelled six (6) subjects and two (2) alternates. Two subjects were lost due to non-compliance with protocol or lack of interest. One panelist was lost due to mechanical data loss. The gender and ages of the subjects who completed the test are 4 females (48 to 56) and 1 male (49).

The Evaluation Method

We evaluated the subjects three different ways:

1. Visual Evaluation by four (4) evaluators who made gross visual comparison of the appearance of wrinkling as seen on the left (treated) side vs. the appearance of wrinkling on the right (untreated) side. The Evaluators used a score of 0 to 4 with "No change" being '0' to "difference visible at a distance" being '4'.

2. Wrinkle count based on analysis of 'before' and 'after' digital photographs of the treated side of the face (orbital area).

3. Wrinkle length based on analysis of 'before' and 'after' digital photographs of the treated side of the face (orbital area).

Results

1. Visual Evaluation: All evaluators recorded clearly visible improvement in three (3) out of five (5) panelists. One subject showed no difference and one subject received a mixed (50/50) evaluation.

2. Wrinkle Count: This is a count of completely disappeared wrinkles. Three (3) out of the six (6) panelists showed a decrease in the total number of whole wrinkles counted. The aggregate loss in wrinkles in the 4-week period of the test was 15/46 or a 32% overall reduction in the appearance of whole wrinkles.

3. Wrinkle Length: This is a measurement of wrinkles that were diminished but not gone. Two (2) subjects who received positive visual evaluation did not show a decrease in wrinkle count. In one case this was due to deep wrinkling. This subject showed a 26% shortening of wrinkles in the treated area. In the second case, the wrinkle lengths were not shorter but a visual reevaluation of the subject verified a visible improvement.

Results:

Visible improvement was observed in 60% of the subjects (Visual Evaluation). For 33% of the test subjects, some of the wrinkles in the treated area disappeared completely (Wrinkle Count). The oldest subject with deep wrinkles showed a 26% shortening in Wrinkle Length in the treated area. Improvements were seen in 66% of post-menopausal subjects; with visible differences in eye area wrinkles beginning two weeks after treatment began. In pre-menopausal women (1 subject), the improvements observed were a 67% reduction in Wrinkle Count and a 25% reduction in Wrinkle Length in the single test subject. In the sole male subject using the active ingredients in a cream formulation, the improvement observed was a 65% reduction in Wrinkle Count. The rapidity and degree of diminution of skin wrinkling observed as described above was unexpected.

EXAMPLE 5

Diminution of Photoaging

As described in Example 4, a composition specifically for diminishing, avoiding or preventing photoaging is prepared according to this invention, and is preferably applied to the skin area anticipated to be exposed to the sun prior to such exposure. The composition need not, but may, in addition, include agents such as those disclosed according to U.S. Pat. No. 6,130,254, to act as blockers of UVA and UVB.

What is claimed is:

1. A composition for preventing or reducing skin aging and wrinkling, which comprises at least one matrix metalloproteinase inhibitor (MMPI) and at least one estrogen or phytoestrogen, wherein said MMPI is Ilomastat.

2. A composition comprising Ilomostat and a triterpenoid glycoside in an amount effective to treat, aging of skin.

3. A composition comprising Ilomastat and a triterpenoid glycoside in an amount effective to treat photoaging of skin.

4. A composition comprising Ilomastat and a triterpenoid glycoside in an amount effective to treat smoking induced wrinkling and fine lines in living human skin.

* * * * *